United States Patent [19]
Gill

[11] Patent Number: 5,750,112
[45] Date of Patent: May 12, 1998

[54] CANINE CORONAVIRUS VACCINE FROM FELINE ENTERIC CORONAVIRUS

[75] Inventor: Michael A. Gill, Burnsville, Minn.

[73] Assignee: Solvay Animal Health, Inc., Mendota Heights, Minn.

[21] Appl. No.: 163,922

[22] Filed: Dec. 8, 1993

Related U.S. Application Data

[63] Continuation-in-part of Ser. No. 24,165, Feb. 26, 1993, abandoned.

[51] Int. Cl.$^6$ .................. A61K 39/02; A61K 39/215; A61K 39/155; A61K 38/00
[52] U.S. Cl. .................. 424/221.1; 424/184.1; 424/201.1; 424/202.1; 424/204.1; 424/225.1; 424/233.1; 424/213.1; 424/211.1; 424/207.1; 424/818; 424/828; 424/223.1; 435/235.1; 435/236; 435/238; 514/888; 514/868; 514/2
[58] Field of Search .................. 424/89, 92, 184.1, 424/818, 221.2, 828, 204.1, 225.1, 223.1, 211.1, 233.1, 207.1, 201.1, 213.1, 202.1; 435/235.1, 236, 238; 514/888, 868, 2

[56] References Cited

U.S. PATENT DOCUMENTS

| | | |
|---|---|---|
| 3,143,474 | 8/1964 | Froelich et al. . |
| 4,567,042 | 1/1986 | Acree et al. . |
| 4,567,043 | 1/1986 | Acree et al. . |
| 4,824,785 | 4/1989 | Acree et al. . |
| 4,904,468 | 2/1990 | Gill . |
| 5,013,663 | 5/1991 | Acree et al. . |
| 5,047,238 | 9/1991 | Acree et al. . |
| 5,200,179 | 4/1993 | Bordt et al. . |
| 5,232,694 | 8/1993 | Baxendale et al. . |
| 5,374,424 | 12/1994 | Kelsey et al. . |
| 5,460,815 | 10/1995 | Olsen . |

FOREIGN PATENT DOCUMENTS

| | | |
|---|---|---|
| 310316 | 5/1989 | European Pat. Off. . |
| 0386946 | 9/1990 | European Pat. Off. . |

OTHER PUBLICATIONS

Appel et al. 1980. Canine Practice. 7(4):22–36.
McGhee et al. 1992. Vaccine. 10(2): 75–88.
Horzinek et al. 1982. Infection and Immunity, 37(3): 1148–55.
Fiscus et al. 1985. J. Clin. Microbiol. 22(3): 395–401.
Corapi et al. 1992. J. Virology. 66(11):6695–6705.
Enjuanes et al. ©1990. In: Coronaviruses & Their Diseases Ed. Cavanagh et al pp. 159–172. Plenum Press N.Y.
Reed et al. ©1994 IN: Coronaviruses. Eds: Laude et al pp. 17–21. Plenum Press, N.Y.
Pedersen et al. 1978. Archives of Virology. 58: 45–53.
Pedersen, et al., Am. J. Vet. Res., vol. 45, pp. 2580–2585 (Dec. 1984).
Pedersen, et al., Am. J. Vet. Res., vol. 42, pp. 368–377 (Mar. 1981).
Ingersoll, et al., Am. J. Vet. Res., vol. 49, pp. 1472–1479 (Sep. 1988).
Hohdatsu, et al., Arch. Virology, vol. 117, vol. 117, pp. 85–95 (1991); and
Evermann, et al., Companion Animal Practice, vol. 19, pp. 6–12 (Spring 1989).

Primary Examiner—N. M. Minnifield
Attorney, Agent, or Firm—John P. White

[57] ABSTRACT

This invention provides a vaccine which contains, per dose, an effective immunizing amount of an inactivated feline enteric coronavirus and a suitable carrier. The vaccine of this invention may also contain an adjuvant, an effective immunizing amount of a second inactivated virus and a an effective immunizing amount of an inactivated bacteria. Additionally provided by this invention is a method of immunizing a dog against disease caused by canine coronavirus involving administering to the dog a dose of the vaccine of this invention. The method of this invention may also involve administering one or more additional doses of vaccine to the dog, immunizing the dog against disease caused by a second virus and immunizing the dog against disease caused by a bacteria.

19 Claims, 1 Drawing Sheet

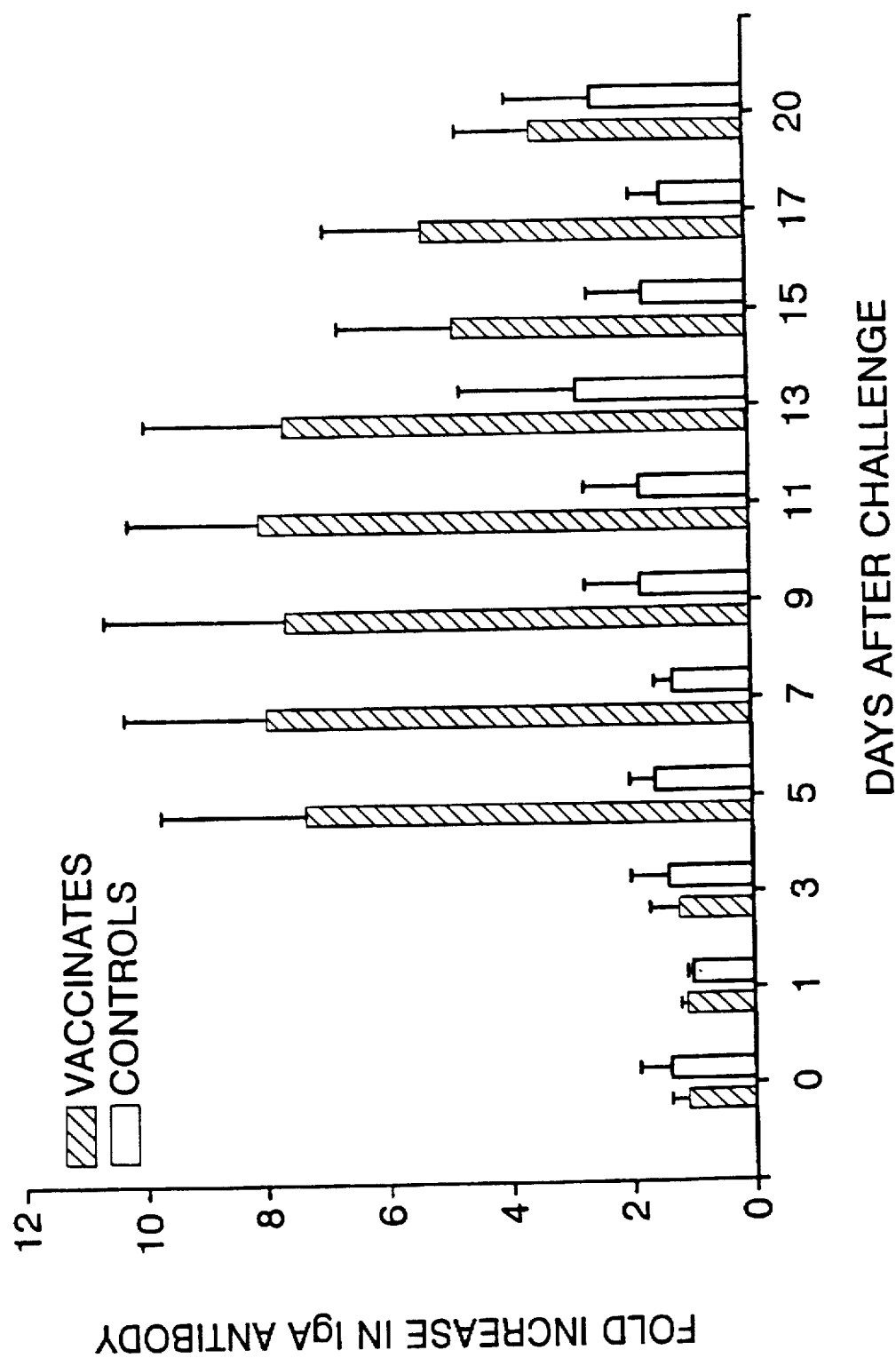

CANINE CORONAVIRUS VACCINE FROM FELINE ENTERIC CORONAVIRUS

This application is a continuation-in-part of U.S. Ser. No. 08/024,165, filed Feb. 26, 1993 now abandoned. Throughout this application various publications are referenced by arabic numerals within parentheses. Full citations for these publications may be found at the end of the specification immediately preceding the claims. The disclosure of these publications in their entireties are hereby incorporated by reference into this application in order to more fully describe the state of the art to which this invention pertains.

BACKGROUND OF THE INVENTION

Coronaviruses belong to the family Coronaviridae and are composed of a single genus of large, enveloped viruses which infect a variety of mammalian and avian species. The virus is heat labile but acid stable which contributes to the ability to survive passage through the stomach. Virions of most coronaviruses contain three proteins; the phosphorylated nucleocapsid protein, N; a small membrane embedded glycoprotein, M; and a large petal-shaped peplomer glycoprotein, S. The M protein is synthesized on ribosomes bound to the rough endoplasmic reticulum and accumulates in the Golgi apparatus and is believed to determine the site of virus budding from the infected cell. The S protein mediates many of the biological properties of the virus, such as attachment to cell receptors, penetration, cell-fusion, and is the major target for virus-neutralizing antibodies. A proportion of the S glycoprotein which is not incorporated into virions is transporter to the plasma membrane of the cell where it remains bound to the surface of the cell.

Canine coronavirus (CCV) was first reported by Binn et al. (1) The isolate was recovered from dogs suffering from diarrhea during an epizootic in Germany. Keenan et al. (2) reported that the isolated virus was capable of inducing intestinal lesions in susceptible neonatal puppies.

CCV gastroenteritis in dogs is highly contagious, and following exposure, the virus rapidly spreads throughout the small intestine. The incubation period is generally 24 to 48 hours but has been as long as one to four days, as reported by Keenan et al. (2) Following oral exposure, the virus enters and colonizes in the upper duodenum. Viral replication results and the infection then proceeds caudally throughout the entire small intestine within days. As a result of the enteritis, the CCV may also spread locally to the regional mesenteric lymph nodes.

The replication of the CCV is localized within the digestive and absorptive cells that are located in the upper two-thirds of the intestinal villi. The viral replication causes death and desquamation of the intestinal epithelial cells resulting in shortening of the intestinal villi. The desquamating cells containing infectious virus are a source of infection for more caudal segments of the intestines and the feces. Loss of digestive enzymes and absorptive capacity results in diarrhea, and dehydration of puppies. Deaths have occurred within as little as 24 to 36 hours after onset of clinical signs despite good supportive care.

Most dogs are afebrile and pathological changes are usually not detected. Puppies are most severely affected and the most common cause of deaths in neonates is from severe dehydration. Severity of the disease can be enhanced when in combination with other enteric canine pathogens (3). Stress, breed and environmental conditions are additional factors that affect the severity of the disease. Animals exposed to CCV develop virus neutralizing (vn) antibody that is detectable in the serum. However, CCV infection is not systemic. Therefore, serum (SVN) antibody titers are indicative of exposure but not of protection. There is no effective antiviral treatment for CCV enteritis. Treatment is supportive with fluid replacement and electrolyte therapy to control emesis and diarrhea and to prevent concurrent infections.

Mucosal immunity appears to play an important role in the protection against CCV enteritis. Appel et al., (4) reported that local immunity, possibly mediated by IgA antibodies in the intestine, was responsible for protection against CCV infection, in a manner similar to transmissible gastroenteritis virus (TGEV) of pigs.

Since 1983, two types of vaccine have been used in an attempt to control disease conditions associated with CCV infections. (5,6) A modified live vaccine introduced in 1983 by Fort Dodge Laboratories, Iowa, intended to protect dogs against CCV was soon demonstrated unsafe and subsequently withdrawn due to adverse reactions. In 1985, an inactivated vaccine to protect dogs against CCV was introduced by Fort Dodge Laboratories and has been shown to be safe and efficacious. Later, another inactivated CCV product was introduced by Smith Kline Beecham to protect dogs against CCV enteritis.

In 1978, the antigenic similarities of CCV, TGEV, feline infectious peritonitis virus (FIPV) and human coronavirus 229 E were reported. (7,8) The close antigenic properties shared by these viruses allowed for the development of serologic assays and experimental vaccines. Another feline coronavirus, feline enteric coronavirus (FECV), has recently been shown to be antigenically related to this group. The dominant antigenic determinants of the S protein are cross reactive between these viruses and afford the opportunity for use as vaccines in the distantly related animal species (9). However, some cross-protection studies with these viruses have offered little protection in the heterologous species (1, 10, 11).

The present invention is directed to a new vaccine composition for protection against CCV. It provides a method of preventing CCV infection in dogs by administering a vaccine prepared from FECV. The immunodominant regions of the S protein of FECV are antiqenically similar to corresponding components on the CCV virion. The S protein of FECV provides a method of preventing CCV in dogs by priming the immunocompetent cells on the mucosal surfaces of the intestine, providing an immunological memory mechanism for protection against CCV infection. In addition, sufficient heterogenicity between the S proteins of FECV and CCV provides an opportunity for the FECV vaccine to overcome levels of CCV maternal antibodies which might neutralize homologous CCV vaccines.

SUMMARY OF THE INVENTION

This invention provides a feline enteric coronavirus vaccine which comprises per dose an effective immunizing amount of a modified feline enteric coronavirus and a suitable carrier. In the presently preferred embodiment of this inventions the modified feline enteric coronavirus is an inactivated feline enteric coronavirus. The vaccine provided by this invention may further comprise an adjuvant in an amount effective to enhance the inmmunogenicity of the modified virus. This invention also provides a vaccine comprising a modified feline enteric coronavirus and a second modified virus. This invention further provides a vaccine comprising a modified feline enteric coronavirus and a modified bacteria.

This invention provides a method of immunizing a dog against disease caused by canine coronavirus which comprises administering to the dog a dose of the vaccine of this invention. Also provided is the method of this invention further comprising administering to the dog one or more additional doses of the vaccine at a suitable interval of time after administration of the preceding dose. The method of this invention may comprise immunizing a dog against disease caused by canine coronavirus and disease caused by a second virus. The method of this invention may also comprise immunizing a dog against disease caused by canine coronavirus and disease caused by a bacteria.

BRIEF DESCRIPTION OF THE FIGURE

FIG. 1: Summary of Mucosal IgA antibody to CCV S-protein levels in fecal samples.

DETAILED DESCRIPTION OF THE INVENTION

This invention provides a feline enteric coronavirus vaccine which comprises per dose an effective immunizing amount of a modified feline enteric coronavirus and a suitable carrier.

For the purposes of this invention, an "effective immunizing amount" of a modified feline enteric coronavirus is any amount of the modified virus effective to immunize a vaccinated animal against disease caused by virulent virus. Typically, the effective immunizing amount of the modified feline enteric coronavirus is an amount which contains greater than about 5 micrograms of S viral antigen. Desirably, the effective immunizing amount of the modified feline enteric coronavirus is an amount which contains from about 5 micrograms to about 7.5 micrograms of the S viral antigen. Example 1D, infra, provides a method for calculating the S viral antigen content of the vaccine composition.

For the purposes of this invention, a "modified" feline enteric coronavirus may be a modified live virus, an inactivated virus, a recombinant virus or a viral subunit. A "modified live" virus is a virulent or attenuated virus capable of eliciting an immune response from a vaccinated animal. As used herein, an "inactivated" virus is a virus which is not capable of infecting an animal's cells, but which can still elicit an immune response from an animal vaccinated with the virus. A "recombinant" virus is a genetically engineered immunogenic virus which is incapable of infecting an animal's cells. The viral subunit vaccine of this invention may comprise the feline enteric coronavirus S glycoprotein in an antigenic form. Thus, this invention contemplates a vaccine comprising an intact virus or an antigenic viral subunit. The effective immunizing amount of the intact virus is the number of viral particles containing an amount greater than about 5 micrograms of the S viral protein. The effective immunizing amount of the subunit vaccine is an amount greater than about 5 micrograms of viral S glycoprotein.

In the presently preferred embodiment of this invention, the modified feline enteric coronavirus is an inactivated feline enteric coronavirus. Feline enteric coronavirus may be inactivated by contacting the virus, as described hereinbelow, with an agent selected from the group consisting of binary ethylenimine, formalin or β-propriolactone. In the presently preferred embodiment of this invention, the feline enteric coronavirus is inactivated by contacting the virus with binary ethylenimine.

"Suitable carriers" for use with a modified feline enteric coronavirus in a vaccine in accordance with the practice of this invention are solutions suitable for suspending modified live viruses and administering to animals. Such suitable carriers are well known to those skilled in the art and include, but are not limited to, aqueous buffers, e.g., phosphate buffers.

The vaccine of this invention may further comprise an adjuvant in an amount effective to enhance the immunogenicity of the modified feline enteric coronavirus. For the purposes of this invention, an "adjuvant" is a composition of matter which enhances the response of an animal's immune system to a viral antigen when the antigen is administered with the adjuvant. The vaccine of this invention may comprise an adjuvant selected from the group consisting of aluminum hydroxide, saponin or aluminum phosphate. In the presently preferred embodiment of this invention, the adjuvant is aluminum hydroxide.

For the purposes of this invention, an "effective amount" of an adjuvant is any amount of the adjuvant effective which, when it is administered with the antigen to an animal, is effective to enhance the animal's immune response to the antigen. Typically, the effective amount of the adjuvant is from about 3% by volume of the dose of vaccine to about 10% by volume of the dose. Desirably, the amount of the vaccine is an amount about 5% by volume of the dose.

Also provided is the vaccine of this invention further comprising an effective immunizing amount of a second modified virus. The second modified virus may be a modified live virus, an inactivated virus, an attenuated virus or a viral subunit, as described hereinabove. The vaccine of this invention may comprise a second modified virus selected from the group consisting of a modified canine distemper virus, a modified canine adenovirus, modified canine parvovirus, modified canine parainfluenza virus or a modified canine herpesvirus.

The vaccine of this invention may further comprise an effective immunizing amount of a modified bacteria, e.g., a modified Leptospira. As used herein, a "modified" bacteria is an intact bacteria capable of eliciting an immune response in an animal to which the modified bacteria is administered, but which is incapable of causing disease in the animal. The modified bacteria may be a modified live bacteria, an inactivated bacteria, or a bacterial subunit, i.e., an antigenic protein derived from the bacteria. For the purposes of this invention, an "effective immunizing amount" of a modified bacteria is any amount of the modified bacteria effective to elicit an immune response in an animal to which the modified bacteria is administered. Effective immunizing amounts of modified bacteria are well known to those skilled in the art or may be readily determined by them without undue experimentation. Typically, an effective immunizing amount of a modified live or inactivated bacteria is an amount greater than about $10^7$ cells/ml, desirably an amount from about $10^7$ cells/ml to about $10^{12}$ cells/ml. Typically, an effective immunizing amount of a bacterial subunit is an amount greater than about 10 micrograms of the bacterial subunit, desirably, an amount from about 10 micrograms of the subunit to about 1,000 micrograms.

This invention provides a method of immunizing a dog against disease caused by canine coronavirus which comprises administering to the dog a dose of the vaccine of this invention. Typically, the dog is at least about six weeks old when the vaccine is administered. Desirably, the dog is from about six weeks old to about nine weeks old when the vaccine is administered. The vaccine of this invention may be administered to the dog by any means generally accepted by those skilled in the art of administering vaccines to dogs. Examples of such means of administering vaccines include, but are not limited to, subcutaneous injection or intramuscular injection.

The method of this invention may further comprise administering to the dog one or more additional doses of the vaccine, each additional dose of vaccine being administered at a suitable interval of time after administration of the preceding dose. The method provided by this invention thus contemplates administering multiple doses of the feline enteric coronavirus vaccine to a dog. Administration of more than one dose of a vaccine is intended to enhance the immune response of the vaccinated animal to viral antigen. Administration of each dose should be separated by an interval of time suitable to allow for an enhanced immune response. A "suitable" interval of time between administration of multiple doses of a vaccine to an animal is therefore any interval of time between administration of doses of a vaccine sufficient to cause the animal to generate a greater immune response than administered a single dose. Typically, the suitable interval of time between administrations of multiple doses of the feline enteric coronavirus vaccine of this invention is from about two weeks to about five weeks. Desirably, the interval of time is from about two weeks to about three weeks.

This invention contemplates administration of a booster dose of the modified feline enteric coronavirus vaccine. Preferably, the booster dose is administered approximately one year after the previous administration of vaccine. Administration of a booster dose of a vaccine to a dog is a generally accepted veterinary practice, designed to insure that the dog remains capable of generating an immune response to viral infection throughout its life.

Also provided is a method of immunizing a dog against disease caused by canine coronavirus and disease caused by a second virus which comprises administering to the dog the vaccine of this invention, wherein the vaccine comprises the modified feline enteric coronavirus of this invention and a second modified virus. The second modified virus may be selected from the group consisting of a modified canine distemper virus, a modified canine adenovirus, a modified canine parvovirus, a modified canine parainfluenza virus or a modified canine herpesvirus.

This invention provides a method of immunizing a dog against disease caused by canine coronavirus and disease caused by a bacteria which comprises administering to the dog a dose of the vaccine of this invention, wherein the vaccine comprises an effective immunizing amount of a modified feline enteric coronavirus and an effective immunizing amount of a modified bacteria. The modified bacteria may, but is not required to be, a modified Leptospira.

This invention will be better understood from the Examples which follow. However, those skilled in the art will readily appreciate that the specific examples detailed are only illustrative of the invention as described more fully in the claims which follow thereafter.

EXAMPLES

Example 1
Vaccine Preparation

As discussed previously, the vaccine of this invention is produced using a modified feline enteric coronavirus which can be a modified live feline enteric coronavirus, an inactivated feline enteric coronavirus, a recombinant feline enteric coronavirus or a viral subunit of a feline enteric coronavirus, each being effective to protect an animal against canine coronavirus. In this example, the preparation of the vaccine using an inactivated feline enteric coronavirus is discussed.

A. Preparation of Cell Cultures

Crandall feline kidney (CRFK) cells, available from the American Type Culture Collection, ATCC No. CCL 94, or a cloned population identified as FK-CU are expanded as monolayers in plastic cell culture vessels in Dulbecco's Minimal Essential Medium (DMEM) supplemented with vitamins, essential amino acids, 2 mg/ml sodium bicarbonate and 0.584 mg/ml L-glutamine [Virology, Vol. 8: p. 396 (1959) and Virology, Vol. 12: p. 185 (1960)]. As a preservative, 30 μg/ml gentamicin is added. Cells are grown in culture vessels to 100% confluency, approximately $2 \times 10^5$ cells per cm$^2$ of growth surface area, using standard cell culture techniques. Generally, plastic roller bottles with a growth surface of 850 cm$^2$, containing 200 ml of DMEM supplemented with 5% fetal bovine serum, and $1.5 \times 10^8$ cells are used for vaccine production. The cell cultures are initiated by seeding approximately $1.5 \times 10^7$ cells into 200 ml of growth medium in a roller bottle on a roller bottle rotator at 0.25 to 2 rpm at 35° C. to 38° C.

B. Inoculation of Cell Cultures with Feline Enteric Coronavirus and Harvest of Cultures Isolates of feline enteric coronavirus, such as the WSU 79-1683 strain, available from the American Type Culture Collection, ATCC No. VR-989, or other suitable feline enteric coronaviruses may be used for manufacturing an inactivated CCV vaccine. Feline enteric coronavirus is received from the ATCC at the ninth cell culture passage is adapted to grow in the feline kidney cell line by two serial passages. The Master Seed Virus MSV X is, therefore, the 11th passage. To establish purity, the Master Seed Virus is tested in accordance with 9 C.F.R. §§ 113.27, 113.28 and 113.55. The passage level of the vaccine is no more than five passages from the Master Seed Virus.

CRFK stock cells are stored at −70° C. or lower. Virus Master Seed is stored at −70° C. Working seed and production seed viruses are stored at −40° C.

For inoculation of the roller bottles with virus, the growth medium is decanted from the monolayers which are 95% to 100% confluent. The medium is replaced with 100 ml of DMEM, without bovine serum, containing sufficient seed virus to achieve a minimum multiplicity of infection (MOI) of 0.01. An 850 cm$^2$ roller bottle contains $1 \times 10^8$ to $4 \times 10^8$ cells. At a MOI of 0.01, $2 \times 10^8$ times 0.01 yields $2 \times 10^6$, which is divided by the antilog of the seed titer. Virus seed and product harvest yield $10^{5.0}$ to $10^{8.0}$ TCID$_{50}$ per ml. Thus, $2 \times 10^6$ divided by $1 \times 10^6$ (antilog of $10^{6.0}$) yields 2 ml of the seed used to add to the 98 ml of maintenance medium covering the cells in the 850 cm$^2$ roller bottle. For 40 such roller bottles, 4000 ml of DMEM containing 80 ml of virus seed would be used as the inoculum.

After decanting the growth medium from the rollers, 100 ml of the diluted virus would be added to each roller bottle. Inoculated cultures are incubated at 35° C. to 38° C. Infection is apparent by the typical cytopathic effect (CPE) on the cell monolayer. The CPE consists of patches of rounded cells. Prior to harvest, cultures can be inspected microscopically and macroscopically and only material that shows no indication of contamination is harvested. The fluids containing virus along with the cellular material are harvested at 48 to 72 hours post-infection without further purification, dispensed in containers and stored at −50° C. or below. For this example, 4000 ml of viral fluids would be stored frozen.

C. Inactivation of Virus

For inactivation, the viral fluids are thawed in a 37° C. water bath, combined in a common container and inactivated by binary ethylenimine (BEI). The BEI solution is prepared by adding 2.05 g of 2-bromoethylamine hydrobromide and 0.8 g of sodium hydroxide to 100 ml of water and incubating in a 37° C. water bath for one hour to cyclize and form the BEI. The BEI solution is added to the viral fluids to a final concentration of 1%, by volume. For this example, the 4000 ml of frozen viral fluids would be thawed and warmed to 37° C. and 40 ml of the BEI is added to the viral fluids. The viral fluids and BEI are mixed thoroughly and incubated at 37° C. for 24 to 48 hours. To confirm complete viral inactivation, two ml of the inactivated viral fluids are tested for the absence of residual live virus by inoculation onto a monolayer of feline cells. The inoculated cells are incubated at 37° C.±2° C. for seven days, then subpassaged. The subpassaged cells are stained with a fluorescein labeled polyclonal or monoclonal antiserum to FECV and examined under an ultraviolet microscope for absence of FECV fluorescence. At the end of the inactivation period, the BEI is neutralized by adding a cold (4° C.±2° C.) sterile 1 molar solution of sodium thiosulfate to the reaction mixture to give a final concentration of 0.25%, by weight. For this example, 10.1 ml of the 1 molar solution of sodium thiosulfate is added to the reaction mixture.

D. Quantitation of the Vaccine

An enzyme linked immunoassay (ELISA) technique was developed according to standard methods and used to calculate the effective immunizing amount of the FECV vaccine. Monoclonal antibodies specific for the peplomer (S) antigen of canine coronavirus and polyclonal antibodies against CCV were prepared according to known methods. (12, 13) ELISA plate wells coated with a monoclonal antibody specific for the peplomer (S) antigen of canine coronavirus is reacted with diluted FECV test samples and subsequently treated with a blocking buffer containing nonfat dry milk. After washing, diluted polyclonal antibody against CCV is added to the wells, the wells were washed again and then goat anti-cat IgG horse radish peroxidase (available from Kirkegaard and Perry Laboratories, Inc. Gaithersburg, Md.) is added. After a third washing, 2,2'-azido-di-[3-ethylbenzthiazoline sulfonate (6)] is added to the wells, and the reaction is stopped by addition of sodium dodecyl sulfate. Absorbance of the color reaction in optical units is read at 405 nm with an ELISA reader. The concentration of the FECV antigen in the test is calculated from a standard curve generated by simultaneous testing of dilutions of a known concentration of FECV. The inactivated FECV vaccine of the invention is standardized by this ELISA technique to contain an S antigen content of at least 5 micrograms.

E. Addition of Adjuvant and Preservative

This standardized vaccine preparation is then adjuvanted by mixing the inactivated viral fluids with aluminum hydroxide, to give a final adjuvant concentration of 5%, by volume. For this example, the standardized product would require the addition of 34,000 ml of physiological saline to the 4000 ml of inactivated FECV fluids for an S antigen content of 5 micrograms. This total volume then would be 38,000 ml and to this, 2000 ml of aluminum hydroxide would be added for a final concentration of 5% by volume. As a preservative, merthiolate is added to the adjuvanted inactivated vaccine to a final concentration of 1:10,000 by volume.

Example 2
Interference Study

To demonstrate that the canine coronavirus vaccine containing feline enteric coronavirus does not interfere with the antibody response to other canine antigens, puppies were vaccinated with the CCV vaccine in combination with a vaccine containing modified live virus and inactivated leptospira antigens. All vaccines were formulated at the minimal release dose.

TABLE 1

Canine Coronavirus Vaccine Interference Study
Antibody response[a] (GMT) post 2nd vaccination[c]:

| Vaccine Group[d] | CDV | CAV$_2$ | CPI | CPV | CCV | Leptospira Canicola | Ictero. |
|---|---|---|---|---|---|---|---|
| DA$_2$PPvL/H$_2$O | Neg. | 724 | 11 | 74 | ND | 41 | 493 |
| DA$_2$PPv/Lepto | 84 | 388 | 24 | 56 | ND | 230 | 800 |
| DA$_2$PPV/H$_2$O | 128 | 549 | 7 | 91 | ND | ND | ND |
| DA$_2$PPVL/H$_2$O | 223 | 891 | 9 | 58 | ND | 264 | 1213 |
| DA$_2$PPVL/AlOH$_3$ | 149 | 380 | 13 | 47 | ND | 429 | 2000 |
| DA$_2$PPvL/CV | 91 | 661 | 7 | 92 | 6 | 566 | 1213 |

[a]antibodies directed against leptospira bacteria and canine viruses: CDV - canine distemper virus, CAV$_2$ - canine adenovirus type 2, CPI - canine parainfluenza virus, CPV - canine parvovirus, CCV - canine coronavirus.
[b]Antibody responses are expressed as virus neutralization titers expect for CPV and leptospira which are expressed as HI and microagglutination titers, respectively.
[c]Animals were vaccinated subcutaneously two times at three weeks apart with a 1 ml dose. Serum was collected at 2 weeks after the second vaccination.
[d]Indicates lyophilized vaccine components and the diluent used for rehydration: D - distemper virus, A$_2$ - adenovirus type 2, P- parainfluenza virus, PV parvovirus, L- leptospira, Cv - coronavirus.

The results presented in Table 1 show that the coronavirus vaccine when used to rehydrate the DA$_2$PPVL vaccine, i.e., a vaccine containing distemper virus (D), adenovirus type 2 (A$_2$), parainfluenza virus (P), parvovirus (PV) and leptospiral bacteria (L), did not interfere with the development of antibody to any of the viral or leptospiral components. Furthermore, no significant difference in antibody titers to any of the fractions was observed in puppies vaccinated with the DA$_2$PPPVL rehydrated with the coronavirus vaccine or when water or adjuvant was used as the diluent.

Example 3
Vaccine Evaluation In Guinea Pigs

The FECV vaccine preparation was evaluated for antigen extinction potency by evaluating dilutions of the standardized vaccine in a laboratory animal model. Undiluted and five-fold dilutions (1:5, 1:25, and 1:125, by volume) of vaccine were prepared in DMEM, without bovine serum. Aluminum hydroxide was added to the vaccine preparations to give a final concentration of 5%, by volume.

Four groups of six guinea pigs each, 350 g size, were each administered two 1 ml doses of the vaccine preparations, intramuscularly, at an interval of 21 days apart. The guinea pigs were bled at the time of vaccination, at the time of second vaccination and at 14 days post second vaccination. Table 2 illustrates the CCV serum-virus neutralization (SVN) antibody titers of the guinea pigs at the different bleeding times.

TABLE 2

Antigen Extinction Potency Evaluation in Guinea Pigs
Serum-virus Neutralization Antibody Titers

| Vaccine | Guinea Pig No. | Pre-Vac. | SVN Antibody Titer Pre-2nd Vac. | Post 2nd Vac. |
|---|---|---|---|---|
| Undiluted | 1-1 | Neg | 8 | 32 |
| | 1-2 | Neg | 8 | 32 |
| | 1-3 | Neg | 8 | 64 |

TABLE 2-continued

Antigen Extinction Potency Evaluation in Guinea Pigs
Serum-virus Neutralization Antibody Titers

| Vaccine | Guinea Pig No. | Pre-Vac. | SVN Antibody Titer Pre-2nd Vac. | Post 2nd Vac. |
|---|---|---|---|---|
| | 1-4 | Neg | 8 | 32 |
| | 1-5 | Neg | 8 | 128 |
| | 1-6 | Neg | 8 | 256 |
| 1:5 | 2-1 | Neg | Neg | 8 |
| | 2-2 | Neg | Neg | 128 |
| | 2-3 | Neg | 2 | 8 |
| | 2-4 | Neg | 2 | 2 |
| | 2-5 | Neg | 2 | 8 |
| | 2-6 | Neg | Neg | 2 |
| 1:25 | 3-1 | Neg | Neg | Neg |
| | 3-2 | Neg | Neg | Neg |
| | 3-3 | Neg | Neg | Neg |
| | 3-4 | Neg | Neg | Neg |
| | 3-5 | Neg | Neg | Neg |
| | 3-6 | Neg | Neg | Neg |
| 1:125 | 4-1 | Neg | Neg | Neg |
| | 4-2 | Neg | Neg | Neg |
| | 4-3 | Neg | Neg | Neg |
| | 4-4 | Neg | Neg | Neg |
| | 4-5 | Neg | Neg | Neg |
| | 4-6 | Neg | Neg | Neg |
| Controls | 5-1 | Neg | Neg | Neg |
| | 5-2 | Neg | Neg | Neg |
| | 5-3 | Neg | Neg | Neg |
| | 5-4 | Neg | Neg | Neg |
| | 5-5 | Neg | Neg | Neg |
| | 5-6 | Neg | Neg | Neg |

All guinea pigs were SVN seronegative at the time of the first vaccination. At the time of second vaccination the undiluted vaccine elicited an antibody response in all guinea pigs. Except for the 1:5 dilution, all other dilutions did not elicit a detectable antibody response at the time of second vaccination. At 14 days post second vaccination, the geometric mean antibody titer of the guinea pigs vaccinated with the undiluted vaccine increased to 64. At this sampling, the geometric mean antibody titer of the guinea pigs vaccinated with the 1:5 vaccine dilution increased to 8. In contrast, guinea pigs vaccinated with the other vaccine dilutions, as well as the controls, remained negative. These data indicate that the guinea pig can serve as a laboratory model for testing FECV vaccines and that the amount of immunizing antigen in the vaccine dose can be diluted beyond a point which stimulates an immune response These data also indicate that FECV elicits an antibody response in guinea pigs which will neutralize CCV antigens.

Example 4

Vaccine Evaluation In Puppies

The same antigenic extinction FECV vaccine preparations were evaluated in young puppies using the gut protection test as a measure of protection. Young healthy puppies determined to be susceptible to CCV, were housed in isolation facilities throughout the duration of the experimental testing. A total of 12 puppies were each vaccinated twice subcutaneously with the vaccine preparation, at an interval of 21 days apart. At 14 days post second vaccination, the vaccinates, along with three nonvaccinated controls, were challenged with virulent CCV.

TABLE 3

Antigen Extinction Potency Evaluation in Puppies
Serum-virus Neutralization Antibody Titers

| Group | Puppy No. | Pre-Vac. | SVN Antibody Titer Pre-2nd Vac. | Post-2nd Vac. |
|---|---|---|---|---|
| Undiluted | 64 | Neg | 4 | 32 |
| | 74 | Neg | 2 | 32 |
| | 82 | Neg | 8 | 64 |
| 1:5 | 66 | Neg | 4 | 32 |
| | 76 | Neg | 4 | 16 |
| | 84 | Neg | 4 | 32 |
| 1:25 | 68 | Neg | 4 | 8 |
| | 78 | Neg | 4 | 4 |
| | 89 | Neg | 4 | 8 |
| 1:125 | 70 | Neg | Neg | 4 |
| | 80 | Neg | 8 | 8 |
| | 83 | Neg | Neg | Neg |
| Controls | 72 | Neg | Neg | Neg |
| | 85 | Neg | Neg | Neg |
| | 88 | Neg | Neg | Neg |

At the time of vaccination, all puppies were seronegative for CCV. At the time of second vaccination, the undiluted, 1:5 and 1:25 vaccines elicited an immune response to CCV in all the vaccinated puppies. Puppy No. 80 was the only puppy vaccinated with the 1:125 dilution which had an antibody titer for CCV. At the time of challenge, all puppies vaccinated with the undiluted, 1:5 and 1:25 dilutions of the FECV vaccine had an anamnestic immune response as indicated by the increase in CCV antibody titers. Two of the three puppies in the 1:125 vaccinated group had antibody titers at the time of challenge. These data indicate that the FECV vaccine elicits an immune response in puppies which is capable of neutralizing CCV. Also, these data illustrate the antigenic extinction of the FECV immunogens in the vaccine.

Example 5

Challenge Experiments

For challenge, each vaccinate, along with three nonvaccinated controls, was administered one ml orally and one ml intranasally of a virulent virus preparation. At five days post challenge, the 15 puppies were euthanized, necropsied and the small intestine removed. The small intestine was divided into 10 segments of equal distance apart and a small sample from each of the segments collected and stored at −70° C. until evaluated. For evaluation, the intestinal samples were sectioned (6 μm thick) on a cryostat, air dried on a glass slide for 30 minutes at 37° C. and then stored at 4° C. until stained. For immunofluorescence, the sections were fixed in cold acetone for 10 minutes and then air dried for 30 minutes at 20° C. prior to staining with diluted fluorescein isothiocyanate conjugated antiserum for 20 minutes at 37° C. in a humidified chamber. After staining, the slides were washed twice (5 minutes each) with phosphate buffered saline (PBS), pH 7.0, and once for 5 minutes with distilled water. Slides were allowed to air dry and examined immediately by ultraviolet microscopy to determine the degree (scale of 1+ to 4+) of CCV antigens in the absorptive cells of the intestinal villi. Table 4 illustrates the results of the gut protection test.

TABLE 4

Antigen Extinction Potency Evaluation in Puppies Gut Protection Test

| Vac. | Puppy No. | 1 | 2 | 3 | 4 | 5 | 6 | 7 | 8 | 9 | 10 |
|---|---|---|---|---|---|---|---|---|---|---|---|
| Undil. | 64 | - | - | - | + | 3+ | 4+ | 2+ | 2+ | 2+ | + |
|  | 74 | - | - | - | + | 3+ | 3+ | 3+ | 2+ | + | + |
|  | 82 | - | - | - | + | 2+ | + | 2+ | + | + | + |
| 1:5 | 66 | - | - | - | - | + | 2+ | 2+ | 2+ | + | - |
|  | 76 | - | - | - | - | + | + | + | + | + | + |
|  | 84 | - | - | - | - | - | - | + | + | - | - |
| 1:25 | 68 | - | - | - | - | + | - | - | - | - | - |
|  | 78 | - | - | - | - | + | + | - | - | - | - |
|  | 89 | - | - | - | - | - | - | - | - | - | - |
| 1:125 | 70 | - | - | - | - | - | - | - | - | - | - |
|  | 80 | - | - | - | - | - | - | - | - | - | - |
|  | 83 | - | - | - | - | - | - | - | - | - | - |
| Cntrl. | 72 | - | - | - | - | - | - | - | - | - | - |
|  | 85 | - | - | - | - | - | - | - | - | - | - |
|  | 88 | - | - | - | - | - | - | - | - | - | - |

These data indicate that sufficient FECV immunogens were present in the undiluted and 1:5 vaccines to prime immunocompetent cells lining the mucosal membranes of the small intestine. The CCV challenge virus entered the gut and limited replication occurred. At the time of necropsy, at five days post-challenge, remnants of the challenge virus were observed by the specific CCV fluorescence present in the absorptive cells lining the villi of the intestine. The 1:25 dilution of the vaccine had insufficient antigen to prime the gut as indicated by the low amount of fluorescence observed in one and two sections from the vaccinated puppies. The 1:125 vaccine dilution failed to prime the gut and the negative fluorescence was comparable to that observed for the control puppies. These data indicate that FECV immunogens can prime the immunocompetent cells lining the intestinal mucosa and protect puppies against gastroenteritis caused by CCV. The FECV immunogens in the vaccine can be diluted beyond protection and must be standardized to have sufficient potency to protect dogs against CCV infection.

Example 6

Immunogenicity Test

A) Materials and Methods

1. Dogs

Beagle puppies were obtained from Harlan Sprague Dawley, Inc. Puppies were six weeks old at vaccination and were seronegative (SVN antibody titers≦2) to canine coronavirus (CCV) canine distemper virus (CDV), canine adenovirus type 2 (CAV-2), canine parvovirus (CPV) canine parainfluenza virus (CPI) and microagglutination titers of ≦10 to *Leptospira canicola* and *L. icterohaemorrhagiae*. Puppies were placed in isolation facilities throughout the duration of the vaccination and challenge test periods.

2. Vaccines/vaccination

Virus fluids were prepared from FECV at the fifth passage from Master Seed Virus on FK-CU cells according to the method disclosed in Example 1, supra. After chemical inactivation of the virus fluids, the coronavirus vaccine was formulated at the minimal immunizing dose of FECV antigen. Each one ml dose contained a 1:10 dilution of inactivated FECV fluids. The coronavirus vaccine was adjuvanted with 5% aluminum hydroxide. Experimental groups included puppies vaccinated subcutaneously or intramuscularly with two one ml does at three weeks apart with the coronavirus vaccine. An additional group of puppies received the coronavirus vaccine in combination with a vaccine composition designated $DA_2PPVL$ which contained the minimum release dose of lyophilized modified live virus components of canine distemper virus (CDV), canine adenovirus type 2 (CAV-2), canine parainfluenza virus (CPI), canine parvovirus (CPV), and the lyophilized killed leptospira bacterin. A group of nonvaccinated puppies served as controls.

3. Serology

Blood samples for serological evaluation of SVN antibody titers were collected before and after vaccination and after challenge with virulent CCV. Determination of SVN antibody to CCV, and CDV and CAV-2 was performed by a microtitration method with flat-bottom 96-well microtiter plates. Two-fold serial dilutions of serum samples were prepared in Dulbecco's Modified Eagle's Medium (DMEM) maintenance medium and an equal volume (50 μl) of the appropriate virus strain containing 100–300 $\log_{10}$ and $TCID_{50}$ was added to each well After 90 minutes incubation at 37° C., an equal volume of an appropriate cell suspension in DMEM+5% FBS added to each well. Plates were incubated for seven days at 37° C. in a humidified carbon dioxide incubator and examined under an inverted microscope for viral cytopathic effect (CPE). SVN antibody to CPI was determined by the hemmadsorption inhibition technique. SVN antibody to CPV was assessed by the fluorescent antibody assay performed in 8-well chamber slides. Antibody titers are expressed as the reciprocal of the highest dilution of serum that completely neutralized the virus. Serum samples were sent by the Veterinary Diagnostic Laboratory, University of Minnesota for evaluation of antibody titers to the leptospira fractions by the microagglutination test.

4. Challenge of puppies with virulent CCV

The CCV-6 was obtained from National Veterinary Services Laboratories (NVSL) in Ames, Iowa. A working stock of the virus containing 7.1 $\log_{10}$ $TCID_{50}$/ml was prepared by passage of the virus on the certified FK-CU cell line and stored frozen at −70° C. Animals were challenged according to instructions of NVSL. At two weeks post second vaccination, puppies were challenged with challenge virus diluted 1:100 in DMEM. Each puppy received 1 ml intranasal and 1 ml orally to give a total challenge volume of 2 ml containing a theoretical dose of 5.4 $\log_{10}$ $TCID_{50}$. Titration of the diluted challenge virus resulted in an actual challenge dose of 5.1 $\log_{10}$ $TCID_{50}$. Fecal samples were collected daily throughout the 21 day post challenge period.

5. Gut protection assay

The gut-protection assay was performed essentially as described by Acree et al. in U.S. Pat. No. 4,567,042 and U.S. Pat. No. 4,567,043. On day 21 post challenge, puppies were euthanized and necropsied to harvest the intestinal tract. Ten segments, each of approximately 10 cm in length were taken from the pyloric valve to the large intestine. The sections were placed in mounting fixative and frozen at −70° C. Thin sections were prepared on a microtome, air dried on glass slides and fixed and stained with fluorescein-labeled goat anti-cat IgG (H+L) antibody. Sections were examined with a UV microscope. The degree of fluorescence in each section was indicative of the amount of CCV antigen. Fluorescence intensity was scored − for negative and from ± to 4± for positive and assigned values of 0 for negative and 0.5 to 4 for positive. Total scores were used to calculate a protective index.

6. Isolation of CCV from feces post challenges

A 30% suspension of each fecal sample was prepared in PBS. The material was vortexed vigorously to break up clumps, centrifuged at 1200×g for 15 minutes at 4° C. to pellet debris. The supernatant was filtered through a 0.2 µm filter and 200 µl of each sample was added to a well of 24-well plates containing a 24-hour monolayer of feline cells. Cultures were incubated at 37° C. in $CO_2$ incubator for seven days. To circumvent the problem of toxicity associated with fecal material and increase the chances to isolate virus, 100 µl was removed from each well after four days incubation, and subcultured to 24-well plates containing fresh 24-hour cultures of feline cells. The second set of 24-well cultures were incubated at 37° C. in a $CO_2$ incubator. Both sets of cultures were examined for CCV-characteristic CPE after four and seven days incubation. Cultures that exhibited CPE in the initial 24-well culture or in the subculture were scored as positive. Positive cultures were confirmed as canine coronavirus by immunofluorescence. The total number of samples tested in the initial and subculture plates was used to calculate percentage of puppies shedding CCV in feces (% positive)

7. Detection of mucosal antibody specific for the S-protein of CCV by ELISA

Wells of 96-well microtiter plates were coated with 100 µl of an optimal concentration of a monoclonal antibody to S-protein of CCV or 100 µl of uninfected cell control antigen for 18 hours at 4° C. Wells were washed with PBS-0.5% Tween 20 PBS-Tw and post-coated with PBS containing 2% bovine serum albumin (PBS-BSA). After 30 minutes incubation at 37° C., aliquots of 50 µl of CCV antigen were added to wells and incubated for 1 hour at 37° C. A 50 µl aliquot of the processed and clarified fecal sample was added to wells containing CCV and cell control antigen. After incubation for 1 hour at 37° C., 50 µl of peroxidase-labeled goat anti-dog IgA, α-chain specific, (Bethyl Laboratories, Inc.) was added. Plates were incubated at 37° C. for 1 hour, washed and 100 µl of ABTS substrate (Kirkegaard & Perry Laboratories, Inc.) was added to the wells. After incubation at room temperature for 15-30 minutes, absorbance values were determined on an ELISA reader at 405 nm. Absorbance values from cell control antigen wells were subtracted from absorbance of CCV antigen wells and divided by the background absorbance value. Results were expressed as the fold-increase in antibody levels.

8. CCV SVN activity in fecal samples

Fecal samples that had been processed for virus isolation were tested for VN activity to CCV. Prior to use in the test, the filtered fecal sample was treated with binary ethyleneimine (BEI) to inactivate residual CCV. The BEI was neutralized by the addition of sodium thiosulfate and the sample was tested in the CCV SVN assay B. Results Serum SVN antibody titers post vaccination and challenge Immunogenicity of the coronavirus vaccine was demonstrated by the development of SVN to CCV in vaccinated puppies. Puppies vaccinated at six weeks of age with two does of coronavirus vaccine formulated at the minimum immunizing dose developed SVN antibody to CCV (Table 5). There was no difference in SVN antibody titers to CCV in puppies vaccinated by either the subcutaneous or intramuscular route. Puppies vaccinated with the coronavirus vaccine in combination with vaccine containing a full antigen dose of CDV, CAV-2, CPI, CPV and L. canicola and L. icterohaemorrhagiae developed SVN antibody titers to CCV that were similar to puppies that received the coronavirus vaccine alone. All nonvaccinated control puppies remained seronegative to CCV throughout the experimental vaccination period. When puppies were challenged with virulent CCV, a booster response CCV SVN titers was observed in all vaccinated puppies. Even the vaccinate that was seronegative after the second vaccination had a SVN titer similar to the other vaccinates post challenge. CCV SVN titers in all nonvaccinated puppies did not increase above 8 after challenge.

TABLE 5

Canine Coronavirus Vaccine
Killed Virus
Immunogenicity Study
Serum Virus Neutralization Antibody Titers

| Dog # | Vaccine | Serum SVN antibody titers | | | |
|---|---|---|---|---|---|
| | | Pre-Vac | Pre-2nd Vac | Pre-Chlg. | Post Chlg.[1] |
| 839 | CV (sc) | Neg. | Neg. | 8 | 32 |
| 862 | | Neg. | Neg. | 2 | 16 |
| 855 | | Neg. | Neg. | Neg. | 16 |
| 868 | | Neg. | Neg. | 4 | 32 |
| 850 | | Neq. | Neg. | 2 | 64 |
| | GMT | Neg. | Neg. | 3 | 29 |
| 856 | CV (im) | Neg. | Neg. | 4 | 32 |
| 857 | | Neg. | 4 | 4 | 32 |
| 848 | | Neg. | Neg. | 4 | 32 |
| 851 | | Neg. | Neg. | 2 | 64 |
| 858 | | Neg. | Neg. | 4 | 32 |
| | GMT | Neg. | Neg. | 4 | 38 |
| 866 | CV (sc) | Neg. | Neg. | 8 | 16 |
| 841 | with | Neg. | Neg. | 8 | 16 |
| 864 | DAPPvL[2] | Neg. | Neg. | 2 | 16 |
| 847 | | Neg. | Neg. | 8 | 16 |
| 845 | | Neg. | Neg. | 4 | 32 |
| | GMT | Neg. | Neg. | 5 | 19 |
| 854 | Controls | Neg. | Neg. | Neg. | 8 |
| 849 | | Neg. | Neg. | Neg. | 8 |
| 860 | | Neg. | Neg. | Neg. | 8 |
| 853 | | Neg. | Neg. | Neg. | 4 |
| 843 | | Neg. | Neg. | Neg. | 4 |
| | GMT | Neg. | Neg. | Neg. | 6 |

[1]Two weeks post CCV challenge.
[2]Vaccine contained the full antigen release dose of CDV, CAV-2, CPI, CPV and L. canicola and L. icterohaemorragiae.

Gut protection assay

Puppies were challenged with virulent CCV at two weeks after the second dose of vaccine Twenty-one days later gut segments were harvested and processed for evaluation in the gut protection assay. The degree of fluorescence in gut sections was proportional to the amount of CCV infection in the intestine. Protection of vaccinated puppies against virulent CCV was determined by a reduction in fluorescence intensity observed in the gut sections. Efficacy of the coronavirus vaccine was assessed by a reduction in florescence intensity of gut sections from vaccinates compared to nonvaccinated controls. Less fluorescence was observed in gut sections from vaccinated puppies than in sections from nonvaccinated control (Table 6). A reduction in fluorescence intensity was observed in gut sections from 14 to 15 (93%) of vaccinated puppies. When fluorescence intensity values were used to calculate fluorescence scores, vaccinates had a mean score of 2.7 compared to a score of 24.3 for the nonvaccinated controls. Fluorescence scores were used to calculate a protective index of 89% for vaccinated puppies. Efficacy of the coronavirus vaccine was not affected by route of administration or by virus and bacterin components in the in the $DA_2PPVL$ vaccine.

TABLE 6

Canine Coronavirus Vaccine
Killed Virus
Immunogenicity Study
Gut Protection Test Fluorescence in thin sections from gut segments[1]

| Dog # | Vaccine | 1 | 2 | 3 | 4 | 5 | 6 | 7 | 8 | 9 | 10 |
|---|---|---|---|---|---|---|---|---|---|---|---|
| 839 | CV (sc) | − | − | − | − | − | − | − | − | − | − |
| 862 | | − | − | − | − | 2+ | ± | ± | ± | 2+ | 1+ |
| 855 | | − | − | − | − | − | − | − | − | − | − |
| 868 | | − | − | − | − | − | − | − | − | − | − |
| 850 | | − | 3+ | 1+ | 1+ | 2+ | 1+ | 1+ | 1+ | 3+ | 2+ |
| 856 | CV (im) | − | − | − | − | − | − | − | − | − | − |
| 857 | | − | − | 2+ | 2+ | − | ± | ± | − | − | − |
| 848 | | − | ± | ± | ± | ± | ± | ± | ± | ± | ± |
| 851 | | − | − | − | − | − | − | − | − | − | − |
| 858 | | − | − | − | − | − | − | − | − | − | − |
| 866 | CV (sc) | − | − | − | ± | ± | − | ± | ± | − | ± |
| 841 | with | − | − | − | − | − | − | − | − | − | − |
| 864 | DA$_2$PPVL | − | − | − | − | − | − | − | − | − | − |
| 847 | | ± | ± | ± | ± | − | ± | + | ± | ± | ± |
| 845 | | − | − | − | − | − | − | ± | ± | − | − |
| 854 | Controls | 1+ | 2+ | 4+ | 2+ | 2+ | 3+ | − | 2+ | 3+ | 3+ |
| 849 | | 3+ | 4+ | 3+ | 2+ | 3+ | 3+ | 4+ | 3+ | 4+ | 2+ |
| 860 | | ± | ± | 1+ | 3+ | 2+ | 3+ | 3+ | 2+ | ± | 2+ |
| 853 | | 4+ | 4+ | 3+ | 3+ | 1+ | 2+ | 1+ | 1+ | 2+ | 2+ |
| 843 | | 3+ | 3+ | 2+ | 2+ | 4+ | 3+ | 3+ | 2+ | 3+ | 3+ |

[1]Degree of fluorescence scored from ± to 4+, or as − for negative, is proportional to the amount of CCV infection.

by culture on feline cells. Cultures were passaged on feline cells to amplify CCV present in the fecal sample and reduce the inherent problem of toxicity associated with fecal material. For up to three days after CCV challenge, CCV was reisolated from approximately the same percentage of vaccinated and nonvaccinated puppies (Table 7). After three days post challenge, fewer vaccinated puppies shed CCV than controls. CCV was isolated from only 13% to 33% of vaccinated puppies on day 5 through 20 post challenge. In contrast, 80% to 100% of the nonvaccinated puppies shed virus from days 3 to 11 throughout the post challenge period. CCV continued to be reisolated from 40% to 100% of the puppies on days 13 through 20 post challenge. Shedding of CCV was reduced in puppies vaccinated subcutaneously and intramuscularly and when the coronavirus vaccine was used in combination with the DA$_2$PPVL vaccine.

TABLE 7

Canine Coronavirus Vaccine
Killed Virus
Immunogenicity Study
Isolation of CCV from Feces Post Challenge

| Dog # | Vaccine | Days post CCV challenge | | | | | | | | | | |
|---|---|---|---|---|---|---|---|---|---|---|---|---|
| | | 0 | 1 | 3 | 5 | 7 | 9 | 11 | 13 | 15 | 17 | 20 |
| 839 | CV (sc) | − | + | − | − | + | + | − | − | − | + | + |
| 862 | | − | + | + | − | − | − | − | − | + | + | + |
| 855 | | − | + | − | − | + | − | + | − | − | NS[1] | − |
| 868 | | − | − | + | − | + | + | − | + | − | − | − |
| 850 | | − | − | + | − | − | − | + | − | − | − | − |
| 856 | CV (im) | − | + | + | − | T[2] | − | − | − | + | − | + |
| 857 | | − | − | + | NS | − | − | − | − | − | − | − |
| 848 | | − | − | + | − | − | − | + | − | − | − | − |
| 851 | | − | − | + | − | − | − | − | − | − | − | − |
| 858 | | − | − | + | − | − | − | − | − | − | − | − |
| 866 | CV (sc) | − | + | + | + | − | + | − | − | − | − | − |
| 841 | with | − | + | T | + | + | + | − | + | − | NS | − |
| 864 | DA$_2$PPVL | + | − | T | T | T | + | + | − | − | − | − |
| 847 | | + | − | T | NS | − | − | + | + | − | − | − |
| 845 | | − | − | + | − | − | − | − | − | − | − | − |
| % positive | | 13 | 40 | 67 | 15 | 27 | 33 | 33 | 27 | 13 | 15 | 20 |
| 854 | Controls | NS | − | + | NS | + | + | + | + | + | + | + |
| 849 | | − | − | + | + | + | − | NS | + | T | + | − |
| 860 | | − | − | + | NS | + | + | NS | − | + | + | + |
| 853 | | + | + | + | + | + | + | NS | − | + | + | − |
| 843 | | − | − | − | + | + | + | + | NS | + | + | − |
| % positive | | 25 | 20 | 80 | 100 | 100 | 80 | 100 | 50 | 80 | 100 | 40 |

[1]No sample.
[2]Toxic.

Isolation of CCV from feces post CCV challenge

Fecal samples collected daily throughout the 21 day post CCV challenge period were tested for the presence of CCV S-protein specific mucosal IgA antibody in fecal samples To determine levels of mucosal antibody to CCV, fecal samples were tested in an ELISA that measures IgA antibody specific for the S-protein of CCV. IgA levels for individual vaccinated and control puppies are presented in Table 8 and a summary of IgA levels is presented in FIG. 1. At five days post CCV challenge, a 4 to 13 fold increase in S-protein specific IgA was detected in fecal samples from vaccinated puppies. At this same time, nonvaccinated control puppies showed a maximum of a two fold increase in IgA. Levels of S-protein specific IgA remained elevated in vaccinated animals through day 13 post challenge. IgA levels gradually decreased in vaccinated puppies after day 14 but remained higher than control puppies. Although IgA levels in some nonvaccinated control puppies increased as much as five fold, the mean IgA levels in these animals remained low. There was little difference in IgA levels among the puppies vaccinated subcutaneously and intramuscularly with the coronavirus vaccine alone and in combination with the DA$_2$PPVL vaccine.

CCV SVN activity in mucosal samples

Fecal samples were also tested to determine the presence of mucosal CCV-neutralizing activity. Since CCV present in the filtered fecal sample may interfere with the CCV used for the SVN assay, fecal samples were treated with BEI to inactivate virus. The sample was then tested for the presence of SVN activity to CCV as described for the CCV SVN antibody assay. Mucosal CCN SVN titers of $\geq 64$ were detected in the feces of several vaccinated puppies and persisted for more than one day (Table 9). Mucosal SVN titers were similar in fecal samples from all three vaccinate groups. As with the mucosal antibody ELISA, mucosal CCV SVN activity was detected in fecal samples from nonvaccinated puppies post CCV challenge. However, mucosal SVN titers in controls were generally lower and varied more day to day and from animal to animal

TABLE 8

Canine Coronavirus Vaccine
Killed Virus
Immunogenicity Study
S-Protein Specific Mucosal IgA Antibody

| | | Fold increase in S-protein specific IgA on days post CCV challenge | | | | | | | | | |
|---|---|---|---|---|---|---|---|---|---|---|---|
| Dog # | Vaccine | 0 | 1 | 3 | 5 | 7 | 9 | 11 | 13 | 15 | 17 | 20 |
| 839 | CV (sc) | 1.0 | 1.0 | 1.0 | NS | 8.9 | 10.2 | 10.8 | 11.5 | 4.9 | 3.3 | 4.6 |
| 862 | | 1.0 | 1.0 | 1.0 | 4.2 | 11.3 | 11.3 | 9.6 | 7.5 | 7.0 | 5.6 | 3.2 |
| 855 | | 1.0 | 1.3 | 1.0 | 8.9 | 9.1 | 7.9 | 10.4 | 9.1 | 4.3 | NS | 2.8 |
| 868 | | 1.0 | 1.0 | 1.0 | 13.1 | 11.9 | 8.9 | 10.4 | 5.8 | 4.9 | 6.5 | 3.5 |
| 850 | | 1.0 | 1.0 | 1.0 | 6.9 | 9.2 | 14.6 | 10.4 | 8.8 | 3.1 | 4.8 | 3.9 |
| 856 | CV (im) | 1.9 | 1.0 | 1.0 | 8.5 | 5.8 | 9.0 | 8.0 | 8.4 | 2.7 | 3.1 | 1.8 |
| 857 | | 1.0 | 1.0 | 1.0 | NS | 10.7 | 8.2 | 10.5 | 11.2 | 9.2 | 2.9 | 2.2 |
| 848 | | 1.0 | 1.0 | 1.0 | NS | 6.6 | 5.4 | 6.7 | 7.8 | 2.4 | 5.0 | 1.7 |
| 851 | | 1.0 | 1.0 | 2.3 | 6.1 | 4.5 | 3.3 | 5.3 | 6.0 | 4.1 | 5.1 | 2.2 |
| 858 | | 1.0 | 1.0 | 1.0 | 6.2 | 8.3 | 6.4 | 5.1 | 6.6 | 4.1 | 6.6 | 3.5 |
| 866 | CV (sc) | 1.0 | 1.0 | 2.7 | 6.0 | 5.3 | 5.2 | 4.8 | 2.5 | 7.9 | NS | 6.0 |
| 841 | with | 1.0 | 1.0 | 1.0 | 4.9 | 8.7 | 4.9 | 8.3 | 6.5 | 4.4 | NS | 3.6 |
| 864 | DA$_2$PPVL | 1.0 | 1.0 | 1.0 | 6.5 | 6.1 | 3.4 | 7.4 | 9.6 | 5.4 | 7.4 | 3.1 |
| 847 | | 1.8 | 1.0 | 1.0 | NS | 5.3 | 8.2 | 5.8 | 7.4 | 3.8 | 7.9 | 4.7 |
| 845 | | 1.0 | 1.0 | 1.0 | 8.4 | 6.3 | 7.1 | 6.1 | 5.7 | 4.3 | 4.9 | 4.8 |
| 854 | Controls | NS | 1.0 | 1.0 | NS | NS | 3.1 | 2.4 | 3.5 | 3.1 | 1.9 | 1.1 |
| 849 | | 1.1 | 1.0 | 1.8 | 1.7 | 1.6 | 2.2 | NS | 1.5 | 2.2 | 1.9 | 2.2 |
| 860 | | 1.8 | 1.1 | 2.3 | NS | 1.1 | 1.0 | NS | 1.0 | 1.3 | 1.0 | 4.6 |
| 853 | | 1.0 | 1.0 | 1.0 | 1.4 | 1.3 | 1.2 | 1.1 | 5.1 | 1.0 | 1.3 | 3.1 |
| 843 | | 2.0 | 1.0 | 1.0 | 2.1 | 1.0 | 1.6 | NS | NS | 1.0 | 1.0 | 1.3 |

TABLE 9

Canine Coronavirus Vaccine
Killed Virus
Immunogenicity Study
Mucosal CCV SVN Activity in Fecal Samples

| | | Days post CCV challenge | | | | | | | | | |
|---|---|---|---|---|---|---|---|---|---|---|---|
| Dog # | Vaccine | 0 | 1 | 3 | 5 | 7 | 9 | 11 | 13 | 15 | 17 | 20 |
| 839 | CV (sc) | 8 | 8 | 8 | 16 | 32 | $\geq 64$ | 16 | 32 | 32 | $\geq 64$ | 32 |
| 862 | | 16 | 16 | 16 | NS | 16 | 32 | 16 | 16 | 8 | 16 | 16 |
| 855 | | 16 | 16 | 16 | 32 | $\geq 64$ | 8 | 16 | 16 | 32 | 32 | T |
| 868 | | T | 8 | 8 | 32 | 8 | $\geq 64$ | 32 | 8 | 32 | 32 | 32 |
| 850 | | 8 | 16 | 8 | 16 | 32 | 16 | 8 | 16 | 32 | 8 | 32 |
| | GMT | 11 | 12 | 11 | 23 | 24 | 28 | 16 | 16 | 24 | 24 | 27 |
| 856 | CV (im) | 8 | 8 | 8 | 8 | T | 32 | 16 | 16 | 32 | 8 | 8 |
| 857 | | 8 | 8 | T | NS | 16 | 32 | 32 | 32 | 32 | 8 | $\geq 64$ |
| 848 | | 8 | 8 | 16 | 32 | 16 | 32 | 32 | 32 | 32 | 8 | 32 |

TABLE 9-continued

Canine Coronavirus Vaccine
Killed Virus
Immunogenicity Study
Mucosal CCV SVN Activity in Fecal Samples

| Dog # | Vaccine | \multicolumn{11}{c}{Days post CCV challenge} |
|---|---|---|---|---|---|---|---|---|---|---|---|---|

| Dog # | Vaccine | 0 | 1 | 3 | 5 | 7 | 9 | 11 | 13 | 15 | 17 | 20 |
|---|---|---|---|---|---|---|---|---|---|---|---|---|
| 851 |  | 16 | 16 | 32 | 8 | 32 | 16 | 16 | 16 | 16 | 16 | T |
| 858 |  | 8 | 16 | 32 | 16 | 16 | 32 | 16 | 16 | 8 | 16 | 8 |
|  | GMT | 9 | 11 | 19 | 14 | 19 | 28 | 21 | 21 | 21 | 11 | 19 |
| 866 | CV (sc) | 16 | ≧64 | ≧64 | 16 | 32 | 32 | 16 | 16 | 32 | 16 | 32 |
| 841 | with | 16 | 8 | 32 | 8 | 16 | 16 | 8 | 32 | 32 | ≦8 | 16 |
| 864 | DA$_2$PPVL | 32 | 16 | 16 | 32 | 16 | 16 | 16 | 32 | ≧64 | 8 | 32 |
| 847 |  | 16 | 32 | ≧64 | 8 | 16 | 16 | 32 | 16 | 8 | 8 | 8 |
| 845 |  | 16 | 16 | 16 | 32 | 8 | 8 | 16 | 8 | 16 | 16 | 16 |
|  | GMT | 18 | 21 | 32 | 16 | 16 | 16 | 16 | 16 | 24 | 7 | 18 |
| 854 | Controls | NS | 8 | 8 | NS | 8 | 8 | 8 | ≦8 | 8 | 8 | 16 |
| 849 |  | 8 | 16 | 32 | 16 | 16 | 8 | ≦8 | 8 | 8 | 8 | T |
| 860 |  | 32 | ≦8 | 32 | NS | 16 | 16 | ≦8 | ≦8 | ≦8 | ≦8 | 8 |
| 853 |  | 8 | 16 | 16 | 32 | T | T | 8 | 8 | 8 | 32 | ≦8 |
| 843 |  | 8 | 8 | 16 | 16 | 8 | 32 | ≦8 | ≦8 | 8 | 8 | ≦8 |
| 843 | GMT | 11 | 7 | 18 | 20 | 11 | 14 | 2 | 2 | 5 | 7 | 4 |

Discussion

CCV enteritis continues to be an important disease of the dog. Although the course of the disease can be mild, factors such as stress, breed and other canine pathogens can enhance the severity of the disease (3). Thus, CCV vaccines are needed to maintain the health of the dog.

A strain of FECV was chosen as a candidate for further vaccine development because of the growth characteristics and antigenicity of the virus. These characteristics facilitated the economic development of an efficacious vaccine prepared from inactivated and adjuvanted FECV fluids. Immunogenicity of the coronavirus vaccine was demonstrated in puppies as young as six weeks of age by the development of CCV SVN antibody. Results showing that similar SVN antibody titers observed in puppies vaccinated by the subcutaneous or intramuscular route indicated the vaccine can be administered by either route. In addition, combination of the coronavirus vaccine with the $DA_2PPVL$ vaccine did not interfere with development of CCV VN antibody. Therefore, the coronavirus vaccine can be used with the routine canine vaccination regimen of virus vaccines and bacterin components.

Although severe clinical disease can be observed in unprotected dogs after natural exposure to virulent field CCV, the CCV challenge virus provided by NVSL does not produce clinical symptoms in normal puppies. Therefore, efficacy of the coronavirus vaccine was evaluated by the gut protection assay described by Acree et al. in U.S. Pat. No. 4,567,042 and U.S. Pat. No. 4,567,043. Fluorescence intensity of gut sections was used as an indicator of a protective response after virulent CCV challenge. The degree of fluorescence observed in the gut sections, was proportional to the level of CCV infection present in the gut segment. Thus, a reduction in fluorescence intensity of gut sections from vaccinated puppies was interpreted as a reduction in virus infection post challenge with virulent CCV. Reduced fluorescence was observed in sections from 14 of 15 (93%) of vaccinated puppies compared to nonvaccinated controls. These results demonstrated the protective ability of the coronavirus vaccine to reduce viral infection after challenge with virulent CCV. An overall protective index of 89% was demonstrated for puppies vaccinated with the coronavirus vaccine alone or in combination with the $DA_2PPVL$ vaccine.

Results from the gut-protection assay indicated reduced CCV infection in vaccinates at the end of the challenge period. However, whether clearance of virulent CCV in vaccinates occurred gradually or at a definitive time point after challenge was not known. Results of the virus isolation study showed that the decrease in the number of vaccinates shedding CCV occurred between three and five days post CCV challenge. The enhanced clearance of virulent CCV from vaccinated puppies persisted throughout the 21 day challenge period. Although nonvaccinated puppies did not exhibit any severe clinical symptoms post challenge, CCV was shed from the majority of nonvaccinated puppies during the entire post challenge period. The shed of virus from nonvaccinated puppies for extended periods of time such as this could predispose the puppy to infection by other more severe canine pathogens.

The mucosal immune response plays an important role in protection against disease caused by enteric viruses. Investigators have reported that stimulation of the gut-associated lymphoid tissue and production of mucosal IgA antibody is the major protective response against TGE virus infection (14, 15, 16). Since CCV infection is not systemic, the mucosal immune response is the predominant mechanism for clearance of CCV from the intestine. Because the S-protein of coronaviruses is major target of SVN antibody, an ELISA was developed that measured levels of mucosal IgA specific for the S-protein. Results of the ELISA demonstrated that in vaccinated puppies, levels of specific mucosal IgA increased more than seven-fold over background by day five post CCV challenge. In vaccinated puppies the amount of mucosal IgA correlated with the protective immune response of mucosal antibody. Mucosal IgA antibody to the S-protein of CCV was detected in nonvaccinated puppies. However, the mucosal immune response in the puppies was not sufficient to reduce shedding of CCV throughout the 21 day post challenge period. Additional evidence as to the protective role of the mucosal immune response was provided by results that showed the presence of CCV SVN activity in the fecal samples. Although the CCV SVN titers in fecal samples varied, in general VN titers were higher and persisted longer post CCV challenge in vaccinates than controls.

The results presented here demonstrate the development of a safe and efficacious coronavirus vaccine. The coronavirus vaccine was efficacious in six week old puppies when administered subcutaneously and intramuscularly and in combination with a vaccine containing the standard virus and bacterin antigen components. Protection of vaccinated puppies against virulent CCV challenge was assessed by the gut-protection assay. Efficacy was demonstrated by reduced CCV infection of gut segments from vaccinated puppies. In vaccinated puppies, the reduction in virus infection in the intestine correlated with reduced virus shedding and elevated levels of S-protein specific IgA.

References

1. Binn et al. Proc. 78th Ann. Mtg., U.S. Anim. Health Assoc. Roanoke Va. October: 359–366 (1974).
2. Kennan et al. Am. J. Vet. Res. 37:247–256 (1976).
3. Everman et al. Comp. Anim. Pract. 2:15–23 (1988).
4. Appel et al., Canine Prac. 7:22–36 (1980).
5. Fulker et al., Canine Prac. 13:18–27 (1986).
6. Martin, Comp. Cont. Educ. Prac. Vet. 7:1012–1017 (1985).
7. Pedersen et al., Arch. Virol. 58:45–53 (1978).
8. Pensaert et al., Arch. Virol. 68:45–52 (1981).
9. Bordt et al., European Patent No. 0 310 316.
10. Reynolds et al., Arch. Virol. 60:161–166 (1979).
11. Woods et al. Vet. Microbiol. 4:11–16 (1979).
12. Oi., V. T., and L. A. Herzenberg, Immunoglobulin-producing hybrid cell lines. In: *Selected Methods in Cellular Immunology*; (Freeman, San Francisco, 1980; B. B. Mishell and S. Shiigi, eds.) pp. 351–372.
13. Harlow, E. and Lane, D., Immunizations, In: *Antibodies, A Laboratory Manual*. (Cold Spring Harbor Laboratory 1988) pp. 53–137.
14. Aynaud, J. M. et al., Vet. Microbiol. 26:227–239 (1991).
15. Saif, L. J. et al., In: *Immunology of Breast Milk* P. L. Ogra and D. H. Dayton, eds. (New York, Raven Press: 1979) pp. 237–255.
16. Saif, L. J., et al. Am. J. Vet. Res. 40:115–117 (1979).

What is claimed is:

1. A method of immunizing a dog against disease caused by canine coronavirus which comprises administering to the dog a dose of a feline enteric coronavirus vaccine comprising an effective immunizing amount of an inactivated feline enteric coronavirus and a suitable carrier.

2. The method of claim 1, wherein the dog is at least six weeks old.

3. The method of claim 1, wherein the dog is from about six weeks old to about nine weeks old.

4. The method of claim 1, further comprising administering to the dog one or more additional doses of vaccine, each additional dose of vaccine being administered at a suitable interval of time after administration of the preceding dose.

5. The method of claim 4, wherein the suitable interval of time is an amount of time from about two weeks to about five weeks.

6. The method of claim 5, wherein the suitable interval of time is an amount of time from about two weeks to about three weeks.

7. A method of immunizing a dog against disease caused by canine coronavirus and disease caused by a second virus which comprises administering to the dog a dose of a vaccine comprising an effective immunizing amount of an inactivated feline enteric coronavirus, an effective immunizing amount of a second inactivated virus, and a suitable carrier.

8. A method of immunizing a dog against disease caused by canine coronavirus and disease caused by a second virus which comprises administering to the dog a dose of a vaccine comprising an effective immunizing amount of an inactivated feline enteric coronavirus, an effective immunizing amount of an inactivated bacteria, and a suitable carrier.

9. The method of claim 1, wherein the effective immunizing amount of inactivated feline enteric coronavirus is greater than 5 micrograms of S viral antigen.

10. The method of claim 9, wherein the effective immunizing amount of inactivated feline enteric coronavirus is an amount from about 5 micrograms to about 7.5 micrograms of S viral antigen.

11. The method of claim 1, wherein the inactivated feline enteric coronavirus has been inactivated by contacting the virus with an agent selected from the group consisting of binary ethylenimine, formalin and β-propriolactone.

12. The method of claim 11, wherein the inactivated feline enteric coronavirus has been inactivated by contacting the virus with binary ethylenimine.

13. The method of claim 1, wherein the vaccine further comprises an adjuvant in an amount effective to enhance the immunogenicity of the inactivated feline enteric coronavirus.

14. The method of claim 13, wherein the adjuvant is selected from the group consisting of aluminum hydroxide, saponin, and aluminum phosphate.

15. The method of claim 14, wherein the adjuvant is aluminum hydroxide.

16. The method of claim 13, wherein the effective amount of the adjuvant is from about 3% by volume of the dose to about 10% by volume of the dose.

17. The method of claim 13, wherein the effective amount of the adjuvant is about 5% by volume of the dose.

18. The method of claim 7, wherein the second inactivated virus is selected from the group consisting of inactivated canine distemper virus, inactivated canine adenovirus, inactivated canine parvovirus, inactivated canine parainfluenza virus, and inactivated canine herpesvirus.

19. The method of claim 8, wherein the inactivated bacteria is inactivated Leptospira.

* * * * *